US005537499A

United States Patent [19]
Brekke

[11] Patent Number: 5,537,499
[45] Date of Patent: Jul. 16, 1996

[54] SIDE-FIRING LASER OPTICAL FIBER PROBE AND METHOD OF MAKING SAME

[75] Inventor: John P. Brekke, Minnetonka, Minn.

[73] Assignee: Laser Peripherals, Inc., Minnetonka, Minn.

[21] Appl. No.: 292,378

[22] Filed: Aug. 18, 1994

[51] Int. Cl.[6] ............................................. G02B 23/26
[52] U.S. Cl. ........................ 385/31; 385/123; 385/147; 385/902; 606/18
[58] Field of Search ............................... 385/31, 33, 36, 385/76–78, 115, 117, 123, 126–128, 146, 147, 902; 372/6; 606/15–18, 27, 28

[56] References Cited

U.S. PATENT DOCUMENTS

| 4,445,892 | 5/1984 | Hussein et al. | 604/101 |
|---|---|---|---|
| 4,672,961 | 6/1987 | Davies | 606/7 |
| 4,740,047 | 4/1988 | Abe et al. | 385/84 |
| 4,842,390 | 6/1989 | Sottini et al. | 385/43 |
| 4,985,029 | 1/1991 | Hoshino | 606/16 |
| 4,986,628 | 1/1991 | Lozhenko et al. | 385/31 |
| 4,994,060 | 2/1991 | Rink et al. | 606/28 |
| 5,078,711 | 1/1992 | Kakami et al. | 606/16 |
| 5,129,895 | 7/1992 | Vassiliadis et al. | 606/6 |
| 5,163,935 | 11/1992 | Black et al. | 606/17 |
| 5,190,538 | 3/1993 | Hussein et al. | 606/17 |
| 5,242,438 | 9/1993 | Saadatmanesh et al. | 606/15 |
| 5,246,437 | 9/1993 | Abela | 606/5 |
| 5,248,311 | 9/1993 | Black et al. | 606/15 |
| 5,253,312 | 10/1993 | Payne et al. | 385/31 |
| 5,254,114 | 10/1993 | Reed, Jr. et al. | 606/15 |
| 5,257,991 | 11/1993 | Fletcher et al. | 606/17 |
| 5,292,320 | 3/1994 | Brown et al. | 606/15 |
| 5,324,282 | 6/1994 | Dodick | 606/15 |
| 5,324,285 | 6/1994 | Cannon | 606/15 |
| 5,342,353 | 8/1994 | Allen | 606/14 |
| 5,342,355 | 8/1994 | Long | 606/27 |
| 5,342,358 | 8/1994 | Daikuzono | 606/45 |
| 5,343,543 | 8/1994 | Novak, Jr. et al. | 385/31 |
| 5,428,699 | 6/1995 | Pon | 385/31 |

Primary Examiner—John D. Lee
Attorney, Agent, or Firm—Burd, Bartz & Gutenkauf

[57] ABSTRACT

A laser optical fiber probe has a silica fiber core with an end terminating in an inclined surface. A silica capsule encloses the end of the fiber and locates the end of the fiber in a gas chamber. Localized heat fuses the end of the fiber opposite the inclined surface to the capsule thereby eliminating secondary light reflections.

45 Claims, 9 Drawing Sheets

FIG. 9
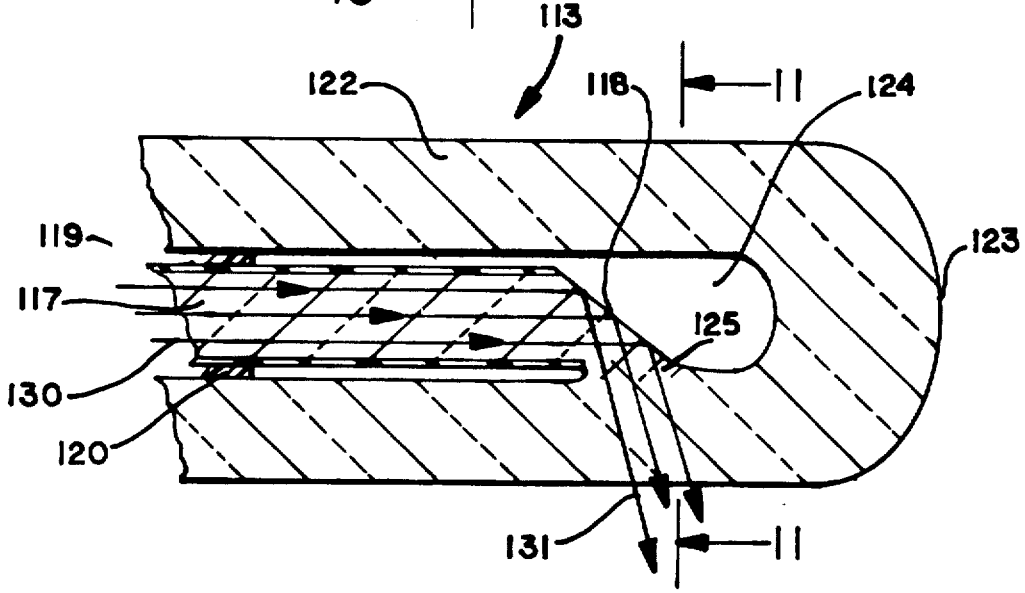
FIG. 10
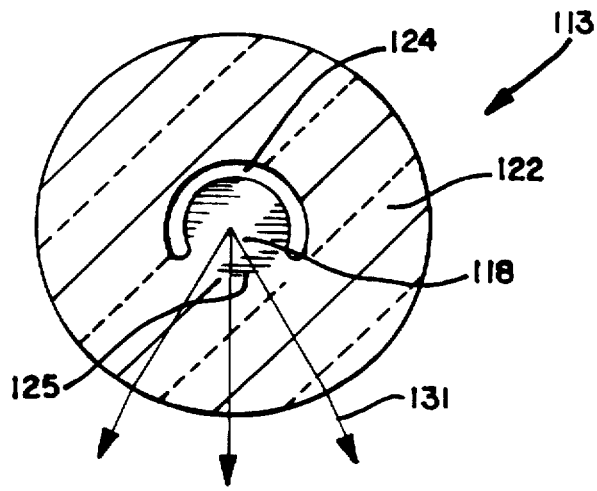
FIG. 11

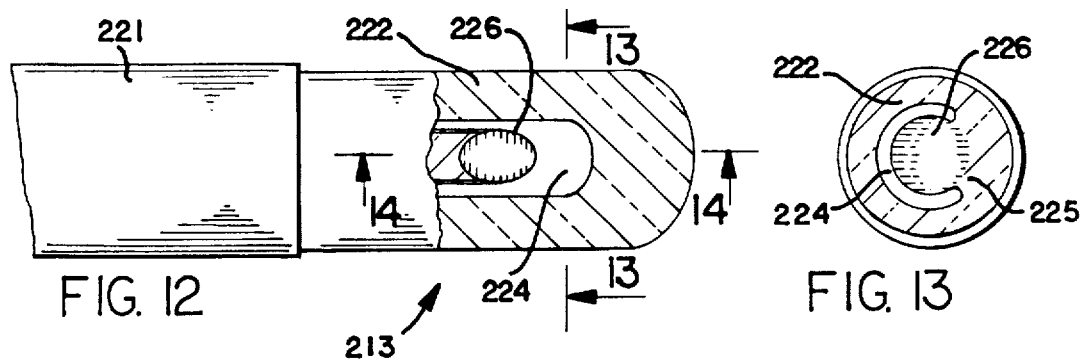
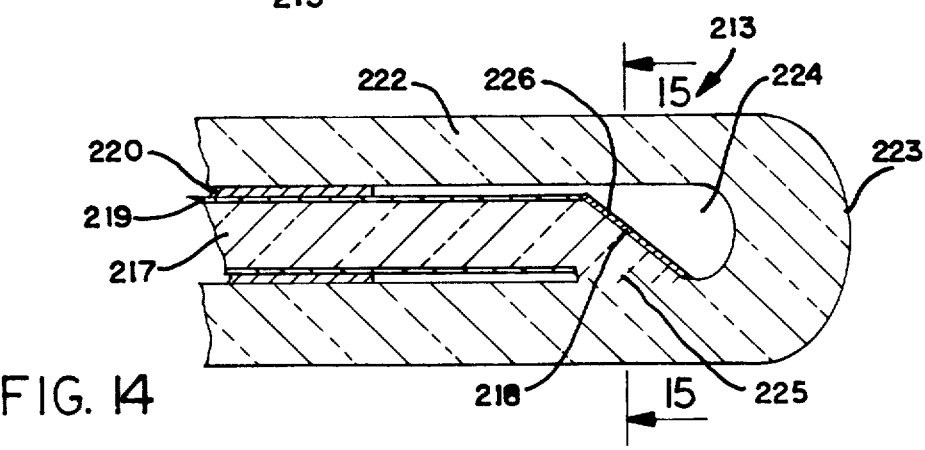
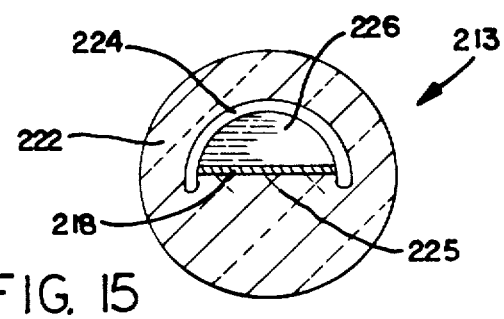
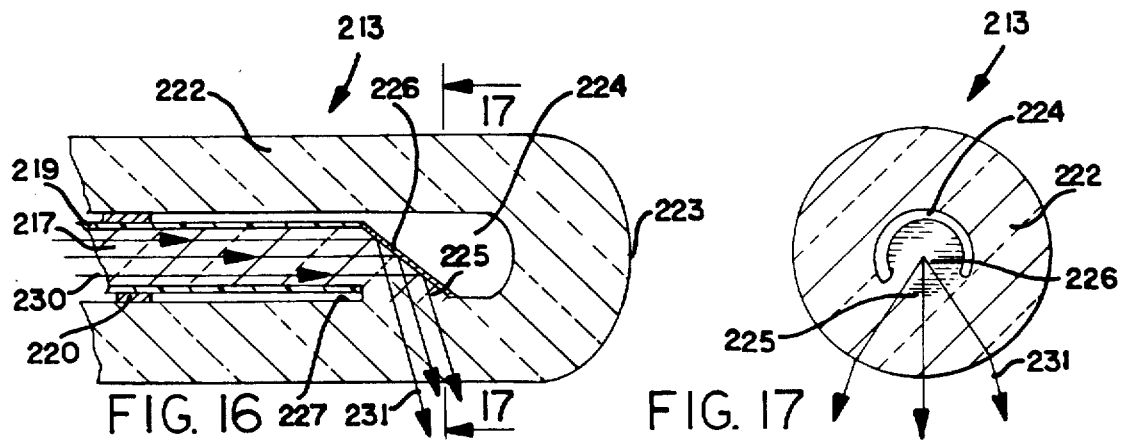

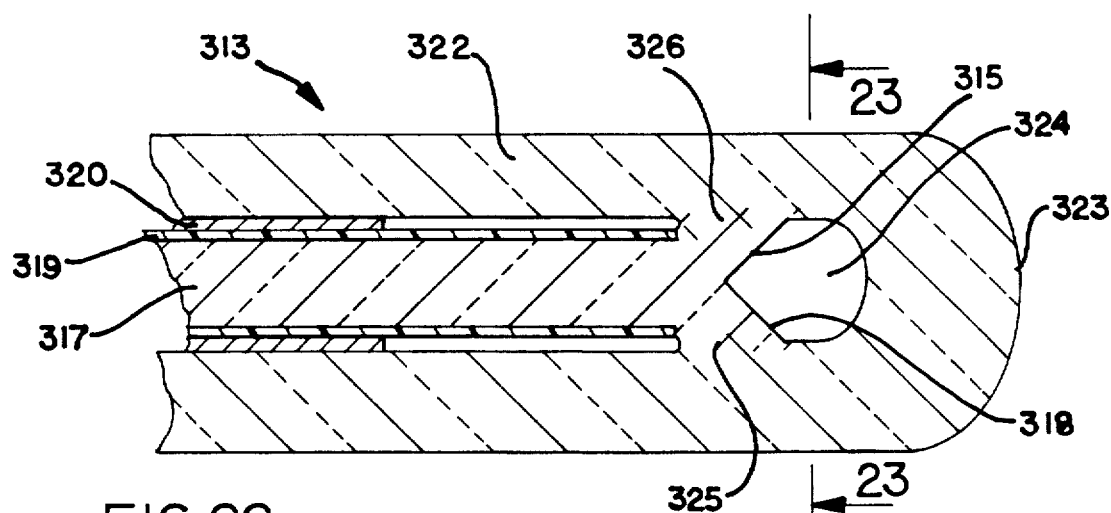
FIG. 22
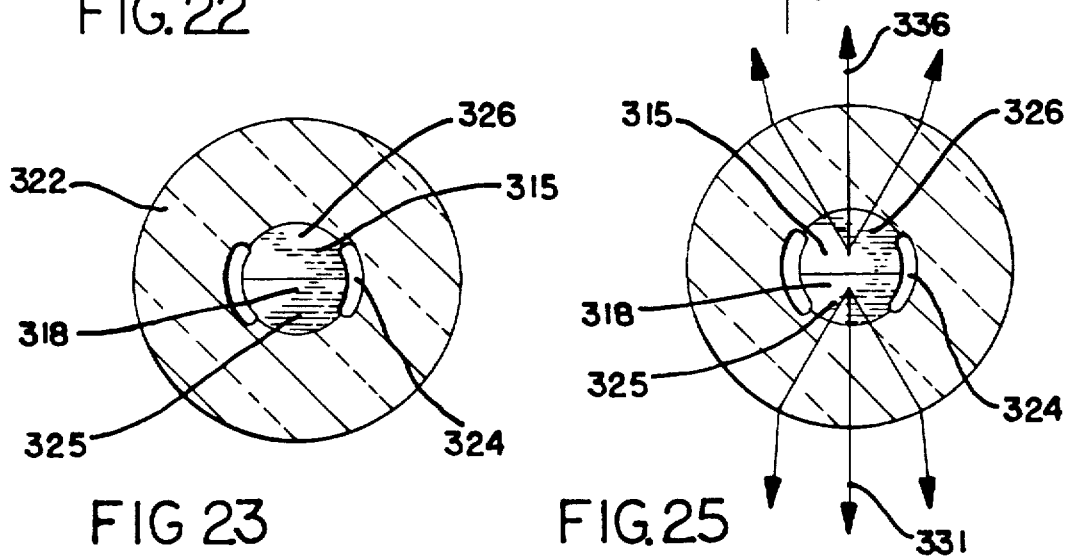
FIG 23
FIG. 25
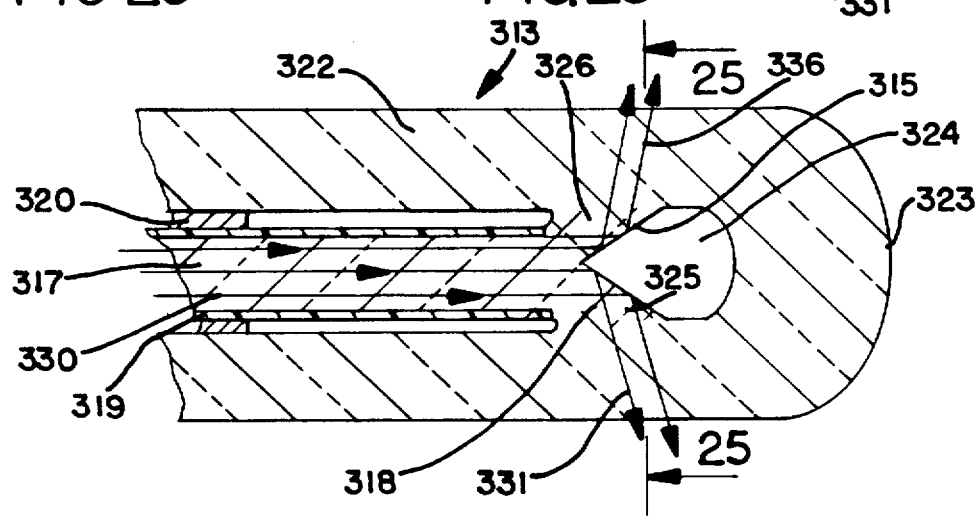
FIG. 24

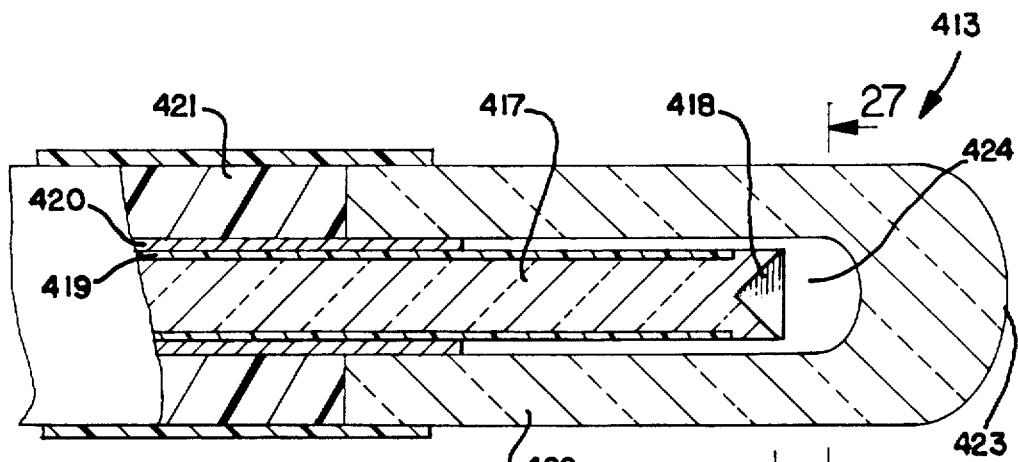
FIG. 26
FIG. 27
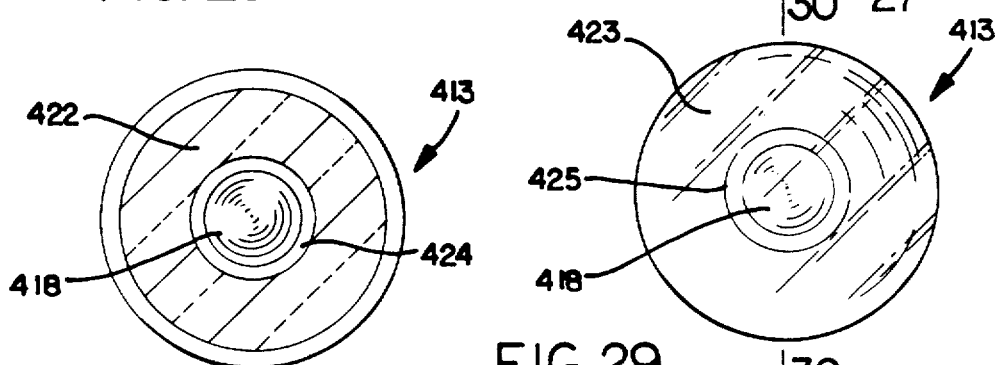
FIG. 29
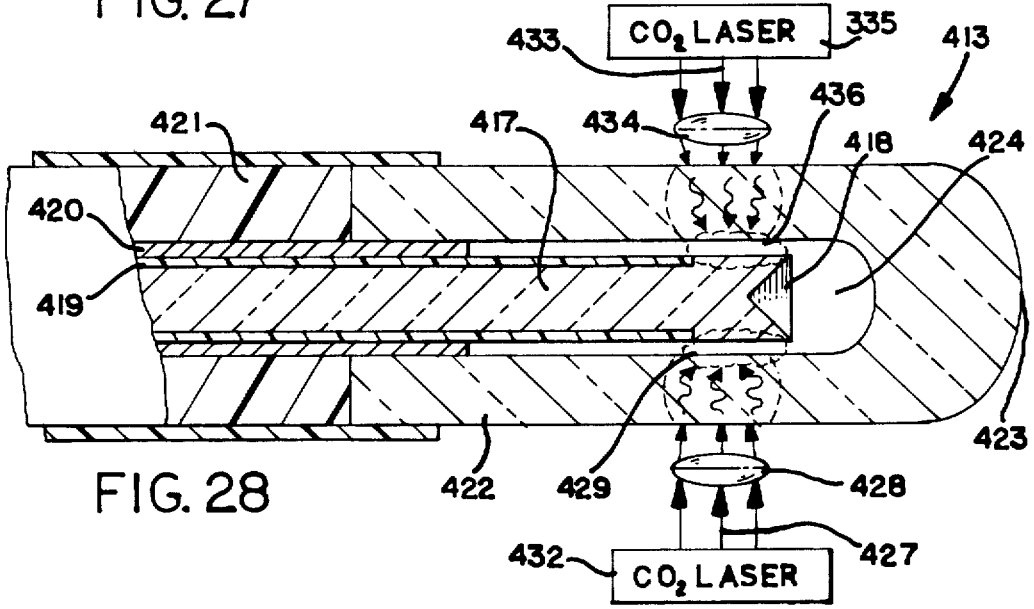
FIG. 28

SIDE-FIRING LASER OPTICAL FIBER PROBE AND METHOD OF MAKING SAME

FIELD OF INVENTION

The invention relates to medical devices used for treating a human body with laser energy transmitted through an optical fiber

BACKGROUND OF INVENTION

Lasers used in medicine and dental application have a light energy output that can be controlled for providing thermal treatment to disease and traumatized tissues. Optical fibers provide a means for delivering laser radiation with minimal energy loss to remote tissue locations within the body. Some therapeutic procedures require that the laser radiation be delivered laterally or generally perpendicular to the fiber optic probe. One system to accomplish the beam deflection uses a gold plated mirror positioned at the distal end of the fiber optic probe. The mirror is held in place by a metal tip. The laser energy is reflected off of the gold surface which must be cooled and kept clean to avoid damage. Another system uses a fiber optic probe that has an angle polish on the distal end thereof. The fiber is placed in a quartz tube to provide a fiber/air interface. An example of the fiber optic probe is disclosed by Vassileadis and Hennings in U.S. Pat. No. 5,129,895. These probes can have a substantial amount of unwanted reflected and refracted laser radiation.

SUMMARY OF THE INVENTION

The invention is a laser optical fiber probe and method making the probe operable to direct light energy laterally of the probe with minimal light scattering and unwanted light reflections. The probe incorporates fresnel light reflections from the optical fiber and air interface laterally into the fiber and capsule enclosing the end of the fiber without secondary light reflections and refractions. The probe is essentially not wavelength selective and operates to deliver high power laser light laterally out of the probe. The probe is usable for therapeutic procedures, such as endoscopic surgery and diagnostic procedures.

The probe includes a laser optical fiber having a distal end with a least one inclined polished surface. The distal end of the fiber can be cut to provide two or more inclined surfaces or provided with a cone-shaped recess forming a cone surface. The surface is polished or covered with coating materials, such as metal film or dielectric materials. A laser beam from a laser propagates down the optical fiber to the inclined surface and is reflected laterally from the surface or coating materials and probe. The distal end of the optical fiber including the inclined surface or coating materials is located in a sealed air chamber provided by a tip or capsule surrounding the end of the optical fiber. A portion of the distal end of the optical fiber opposite the inclined surface is united with heat to the capsule. The heat melts adjacent portions of the fiber and capsule to fuse them together. This eliminates the fiber-air-capsule interfaces that result in undesirable reflected light. The light from the inclined surface is reflected laterally through the combined materials, such as silica, of the fiber and capsule without producing unwanted reflected and refractive light.

A preferred embodiment of the probe has an elongated laser optical fiber of silica enclosed within a cladding of doped fused silica. The distal end of the fiber has an inclined surface polished at an angle of 37 degrees relative to the longitudinal axis of the fiber. The light reflected from the inclined surface, according to fresnels law, emerges at approximately 70 degrees in air with an associated divergence. A capsule comprising a tubular member of silica having a closed end provides support and an air chamber for the distal end of the optical fiber. A portion of the optical fiber opposite the inclined surface is united or fused with heat, 1400° to 1700° C., generated with a carbon dioxide ($CO_2$) laser beam to the adjacent portion of the tubular member. The fusing of the fiber with the tubular member results in common continuous silica from the inclined surface to the exterior of the tubular member. There are no interfaces that reflect and refract light other than the light reflected from the inclined surface. The fusing of the fiber with the tubular member also provides structural support for the tubular member and inhibits removal of the tubular member from the fiber.

The invention includes the methods to manufacture the probe having an optical fiber fused to a tubular member to eliminate unwanted light reflections and refractions. The distal end of the optical fiber is cut at an inclined angle to provide an inclined end surface. The surface is polished at the inclined angle. A coating material, such as a metal film or dielectric material, can be secured to the surface. The distal end of the fiber can be cut at several angles, such as a V-groove, to provide separate inclined surfaces. A cone-shaped recess can be drilled into the distal end of the fiber to provide a cone-shaped surface. A laser beam can be used to cut a general cone-shaped recess in the distal end of the fiber. Longitudinal movement of the laser beam used to fuse the fiber to the tubular member can be used to establish a general cone-shaped recess in the end of the fiber. These surfaces are polished or covered with coating material. The distal end of the optical fiber is longitudinally inserted into a tubular member having a closed end. The inclined surface or coating material is spaced from the inside of the closed end of the tubular member to locate the inclined surface in an enclosed air chamber. Localized high heat, 1400° to 1700° C., generated with laser unites or fuses the silica of the fiber opposite the inclined surface to the silica of the tubular member to join and merge the silica together. During the fusing process, the fusing progress is monitored visually or by instrumentation.

IN THE DRAWINGS

FIG. 9 is a distal end view of the probe of FIG. 8;

FIG. 10 is a sectional view similar to FIG. 8, showing the primary reflective light;

FIG. 11 is a sectional view taken along the line 11—11 of FIG. 10;

FIG. 12 is a top plan view, partly sectioned, of a first modification of the side-firing laser optical fiber probe of the invention;

FIG. 13 is a sectional view taken along the line 13—13 of FIG. 12;

FIG. 14 is an enlarged sectional view taken along the line 14—14 of FIG. 12;

FIG. 15 is a sectional view taken along the line 15—15 of FIG. 14;

FIG. 16 is a sectional view similar to FIG. 14 showing the fiber subjected to laser light and the lateral redirection of the laser light;

FIG. 17 is a sectional view taken along the line 17—17 of FIG. 16;

FIG. 22 is a sectional view taken along the line 22—22 of FIG. 21;

FIG. 23 is a sectional view taken along the line 23—23 of FIG. 22;

FIG. 24 is a sectional view similar to FIG. 22 showing the fiber subjected to laser light and the lateral redirection of the laser light;

FIG. 25 is a sectional view taken along line 25—25 of FIG. 24;

FIG. 26 is a side view partly sectioned of a third modification of the side-firing laser optical fiber probe of the invention;

FIG. 27 is a sectional view taken along the line 27—27 of FIG. 26;

FIG. 28 is a view similar to FIG. 26 showing the fusing of the fiber to the tubular member adjacent the cone surface at the distal end of the fiber;

FIG. 29 is an end elevational view of the probe after the fiber has been fused to the tubular member;

DETAILED DESCRIPTION OF THE INVENTION

Figure 1:
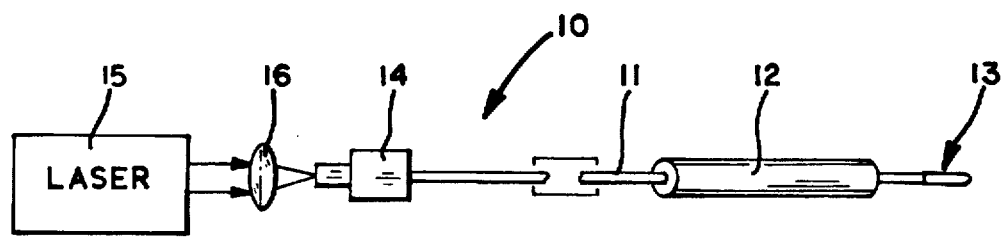
FIG. 1 is a schematic diagram of a laser catheter having a side-firing laser optical fiber probe.
Figure 2:
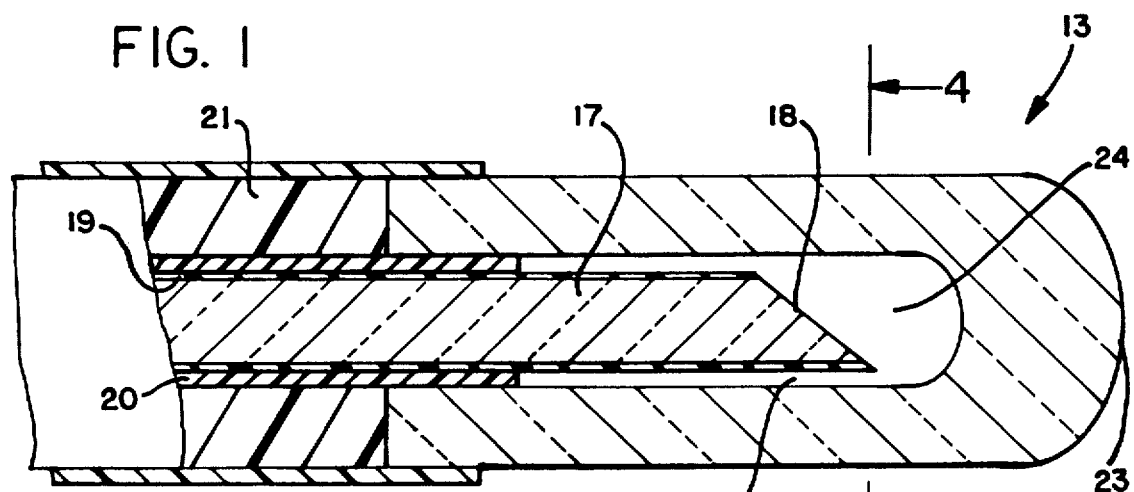
FIG. 2 is a vertical longitudinal sectional view of the distal end of the laser optical fiber probe of FIG. 1.
Figure 3:
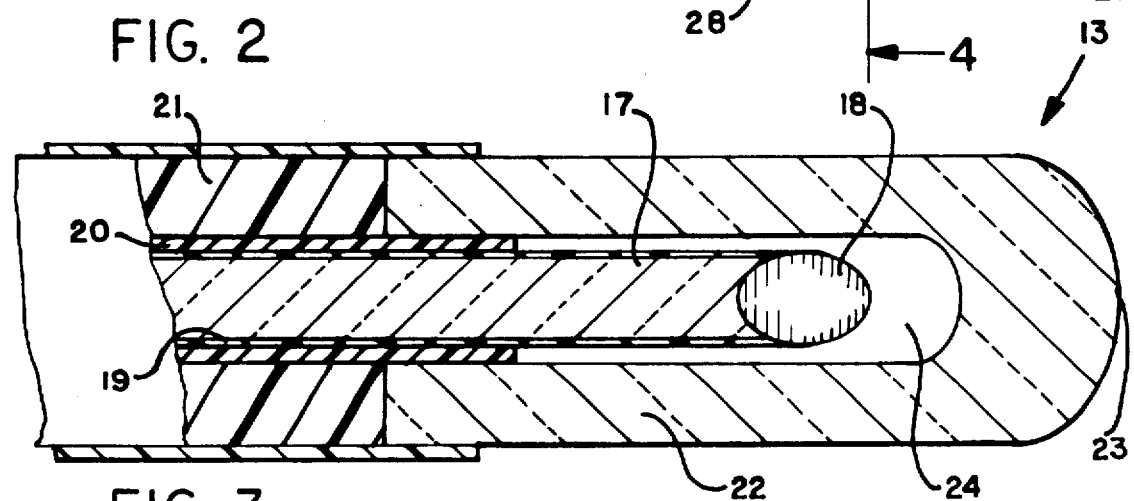
FIG. 3 is a horizontal longitudinal sectional view of the distal end of the laser optical fiber probe of FIG. 1.
Figure 4:
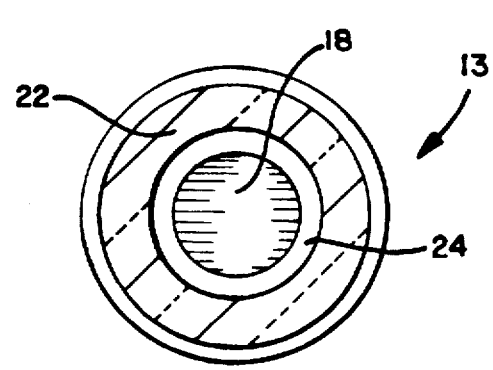
FIG. 4 is an enlarged sectional view taken along the line 4—4 of FIG. 2.

Referring to FIG. 1, there is shown a diagrammatic view of a laser catheter indicated generally at 10, used in radiation medical treatment and diagnostic procedures. Catheter 10 has an elongated flexible optical fiber 11 that is trained through a handle 12 such as an endoscope 12. The distal end of the optical fiber 11 has a probe 13. The optical fiber 11 is joined to a connector 14 that receives light energy from a laser 15 through optical system 16.

Referring to FIGS. 1–6, there is shown a conventional optical fiber probe, indicated generally at 13, for lateral beaming or side-firing of a laser beam. Probe 13 has a central elongated optical fiber 17 made of glass, plastic or fused silica terminating in an end having an inclined flat surface 18. Surface 18 is inclined at about an angle of between 37 and 45 degrees with respect to the longitudinal center line of fiber 17. Surface 18 can be inclined at other angles relative to the longitudinal center line of fiber 17. The inclined angle of the distal end 18 of fiber 17 is 37 degrees. Fiber 17 is enclosed within a cladding 19 of silica material having an index of refraction lower than the index of refraction of the core so as to maintain the laser light in fiber 17. A tubular sleeve 20 of plastic material surrounds layer 19 to protect the integrity of fiber 17. A plastic jacket 21 covers sleeve 20.

A transparent capsule or tubular member 22 secured to jacket 21 surrounds the distal end of fiber 17 including inclined end 18. Member 22 has a generally convex curved closed end 23 and an internal chamber 24 that accommodates a gas, such as air. The distal end of fiber 17, including the inclined end 18, are spaced from the inside walls of tubular member 22 whereby air surrounds the entire distal end of fiber 17.

Figure 5:
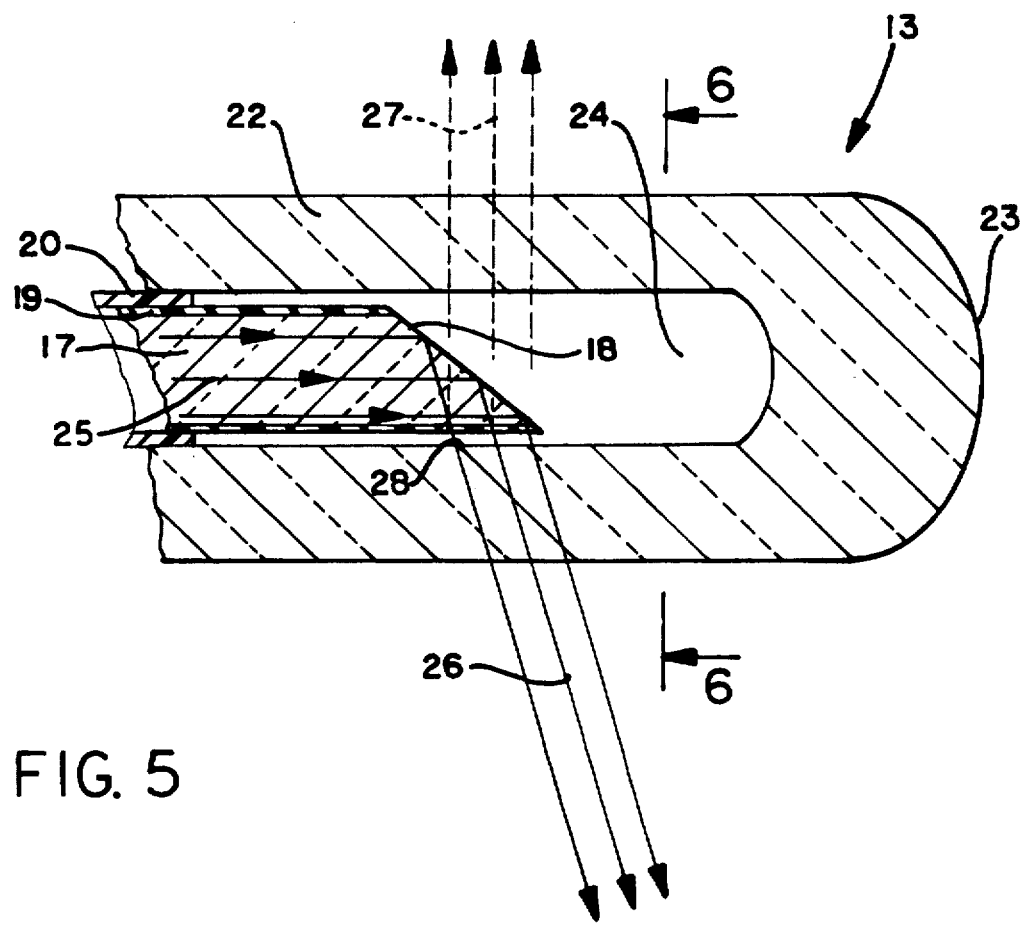
FIG. 5 is an enlarged view of the probe of FIG. 2 showing the primary reflective light and the secondary reflected light.
Figure 6:
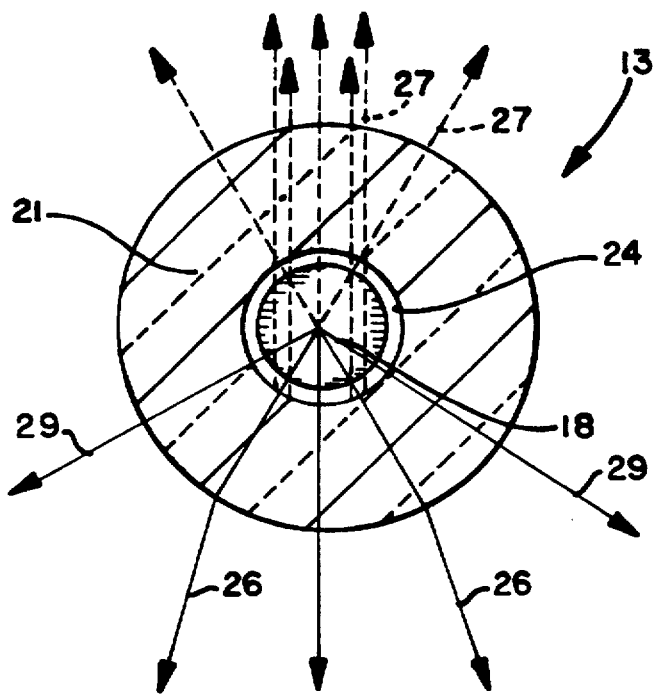
FIG. 6 is a sectional view taken along the line 6—6 of FIG. 5.

In use, referring to FIGS. 5 and 6, laser beam 25 axially propagates along fiber 17 and reflects off of inclined surface 18 as primary reflective light 26, which is directed generally laterally of probe 13. The light 26 must pass through the air chamber 24 and through the material of tubular member 22. Part of the light reflects off of fiber 17 and the inside surface 28 of tubular member 22 and is directed in an opposite direction from the primary reflected light indicated by the secondary reflected light 27. Some of the light from laser beam 27 is additional secondary light 29. As seen in FIG. 6, light 29 is directed outwardly adjacent opposite sides of primary light 26. The reflected light 27 and light 29 are unwanted and potentially unsafe light. This light stems from multiple changes in the refractive indices in the exit path of the laser beam.

Referring to FIGS. 7–11, there is shown the side-firing laser optic fiber probe of the invention, indicated generally at 113. Probe 113 has an elongated flexible optical fiber 117 terminating in an inclined end surface 118. Fiber 117 has a silica fiber core surrounded with a doped fused silica cladding 119. A sleeve 120 of plastic material covers cladding 119. The cladding 119 is enclosed within a jacket (not shown) of plastic material, such as Teflon. Surface 118 has a generally oval polished shape. A diamond-tipped abrasive tool, a carbon dioxide ($CO_2$) laser tightly focused or excimer laser can be used to polish surface 118. These polishing methods are examples of polishing technology for polishing surface 118. Other polishing procedures can be used to create the desired surface characteristics on surface 118. Surface 118 is inclined forwardly at an angle of 37 degrees relative to the longitudinal axis of fiber 117. The inclined angle of surface 118 can be between 37 to 45 degrees relative to the longitudinal axis of fiber 117. Other angles can be used for surface 118. When the angle of surface 118 is 37 degrees, the reflected light will emerge at approximately 70 degrees in air with an associated divergence. A tubular layer of silica cladding 119 surrounds the core of fiber 117 to protect the core and maintain the laser light within fiber 117. A transparent capsule or tubular member 122 of silica having a closed convex curved end 123 is located about the distal end of fiber 117 to enclose the distal end of fiber 117 within an air chamber 124. The distal end of fiber 117 is surrounded by air chamber 124. Member 122 is a silica cylindrical tubular member made of silica material the same as or similar to the silica material of fiber 117.

Figure 7:
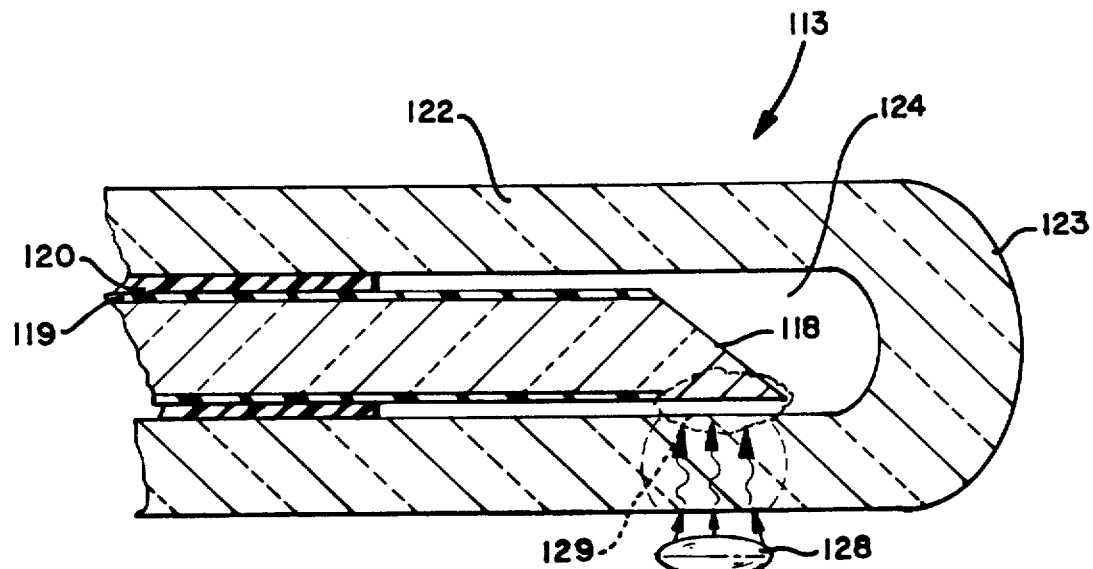
FIG. 7 is a vertical longitudinal sectional view similar to FIG. 2 showing the laser fiber optical probe of the invention.
Figure 8:
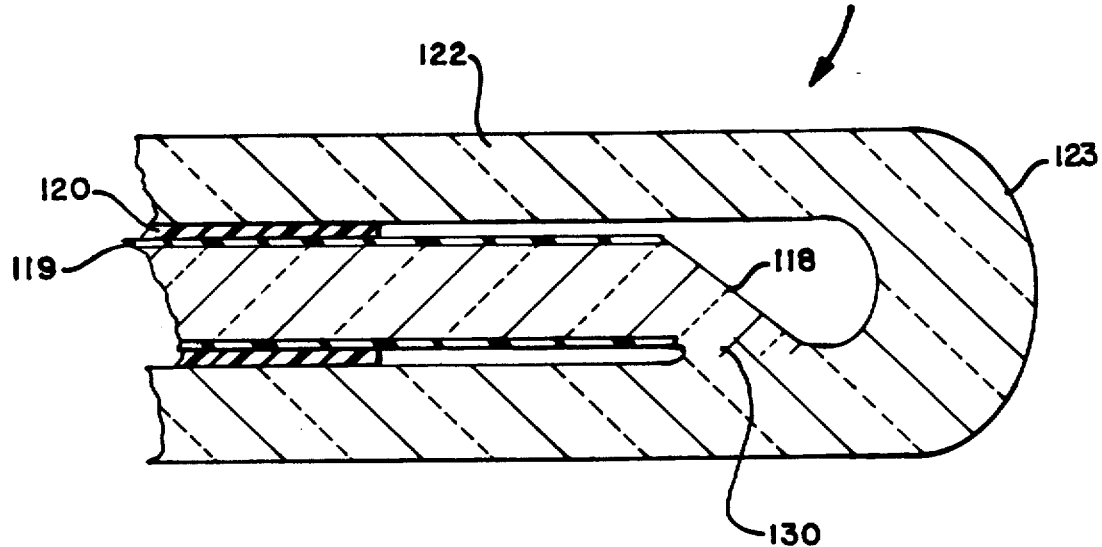
FIG. 8 is a sectional view similar to FIG. 7, showing the optical fiber fused to the tube surrounding the fiber.
Figure 18:
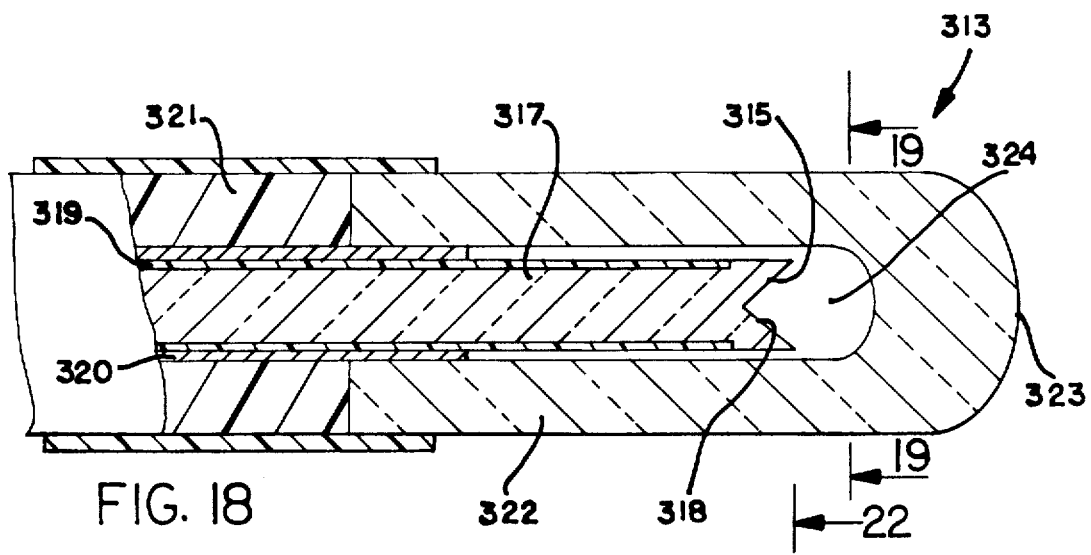
FIG. 18 is a side view partly sectioned of a second modification of the side-firing laser optical fiber probe of the invention.
Figures 19, 21:
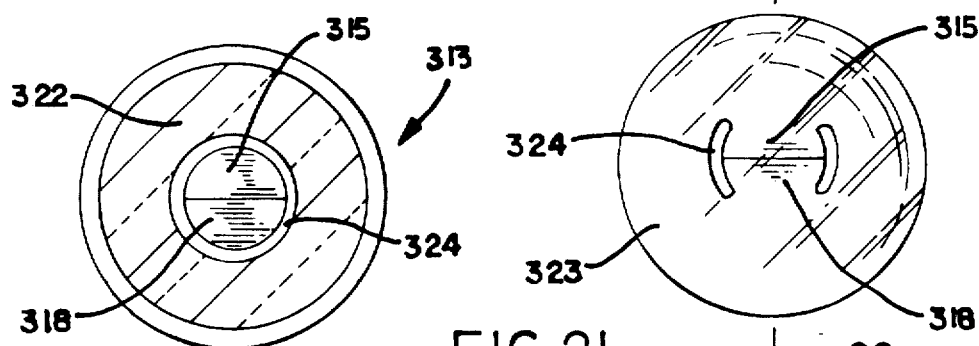
FIG. 19 is a sectional view taken along the line 19—19 of FIG. 18.
FIG. 21 is an end elevational view of the probe after the fiber and tubular member have been fused.

The distal end of fiber 117 is united at 125 to the adjacent inside wall of tubular member 122. The silica materials of fiber 117 and tubular member 122 are fused with localized heat. As shown in FIG. 7, the heat required to cause the fusion of the silica materials of fiber 117 and tubular member 122 is in the range of 1400° to 1700° C. A laser beam 127 directed through an optical lens 128 which concentrates the laser beam on the surface of tubular member 122. The heat from the laser beam 127 is conducted through the silica of tubular member 122 toward the distal end of fiber 117 to the area 129 opposite surface 118. The high temperature heat radiates across the air gap and melts the silica opposite surface 118 as well as the silica of tubular member 122. The silica materials within area 129 are melted and fused together as shown in FIGS. 8–11. Laser beam 127 is generated by a carbon dioxide ($CO_2$) laser 132. Other types of laser energy and heat sources can be used to unite the end of fiber 117 to the inside of tubular member 122.

Probe 133 is made by providing an elongated optical fiber adapted to be coupled to a laser used to direct a laser beam or light along the fiber. The optical fiber has a fused silica fiber core enclosed within a doped silica cladding 119 and a sleeve 120, covered with a plastic jacket. The distal end of fiber 117 is cut at an angle of 37 degrees relative to the longitudinal axis of fiber 117 to provide inclined oval surface 118. Surface 118 is polished with a diamond-tipped abrasive tool, carbon dioxide ($CO_2$) laser, or excimer laser to provide a smooth and flat surface. A silica capsule or tubular member 122, having a closed end 123 and air chamber 124, is provided to accommodate and support the distal end of fiber 117. The distal end of fiber 117 is inserted through the open end of tubular member 122 into air chamber 124. Tubular member 122 is then secured to the sleeve with surface 118 spaced from the closed end 123 of member 122. A heat source 132 generating a carbon dioxide ($CO_2$) laser beam 127 provides heat in the range of 1400° to 1700° C. which is applied to tubular member 122 adjacent the end of fiber 117. The heat is localized on the end of fiber 117 opposite surface 118 and adjacent material of tubular member 122 to unite or fuse fiber 117 to member 122 in area 129 of fiber 117 and tubular member 122 opposite surface 118. As seen in FIGS. 9 and 11, fused area 125 has a circumferential length of about 100 degrees. Other circumferential or arcuate lengths of fused area 125 can be used to connect fiber 117 to member 122. The progress of the fusing process is monitored visually or by instrumentation.

Referring to FIGS. 10 and 11, light or laser beam 130 generated by a laser axially propagates down fiber 117. When light 130 encounters a change in refractive index, it laterally redirects the light energy indicated by arrows 131. The angle of polished surface 118 being 37 degrees relative to the longitudinal axis of fiber 117 results in almost total internal reflection of light 130 as redirected light 131 at an angle of approximately 70 degrees relative to the longitudinal axis of fiber 117. Light 131 is efficiently redirected laterally through the distal end of fiber 117, the fused area 125 and tubular member 122. Fiber 117, fused area 125 and tubular member 122, being of the same silica materials, do not produce changes in the refractive indices and thereby do not produce reflected light nor secondary light. Reflections that stem from multiple changes in the refractive indices in the exit path of the laser beam are eliminated. Probe 113 is a reliable means to efficiently deliver high energy laser light that is essentially not wavelength selective. Probe 113 is used in surgical procedures, such as endoscopic surgery. The laser light directed laterally from probe 113 vaporizes the tissue thereby reducing the size of the tissue gland. Probe 113 is also usable in diagnostic procedures to determine location and size of in vivo tissues. Low level laser light is directed laterally from probe 113 into tissue. The laser light causes the tissue to fluorescence. A portion of this fluorescence is directed back towards probe 113. The probe 113 senses the intensity of the fluorescent light and transmits the light back along the fiber core. Changes in the intensity and spectrum of the reflected light are recorded and analyzed to provide information as to the condition of in vivo tissue.

Referring to FIGS. 12–17, there is shown a first modification of the side-firing laser optical fiber probe of the invention, indicated generally at 213. Probe 213 has an elongated flexible optical fiber 217 terminating in an inclined end surface 218. Coating material 226 attached to surface 218 reflects light laterally of optical fiber 217. Coating material 226 is a film of metal or dielectric material bonded to surface 218. The metal film can be gold, silver or other metals that reflect light. The dielectric material can be several layers of non-conductive materials united to surface 218. Fiber 217 has a silica fiber core surrounded with a doped fused silica cladding 219. Surface 218 and coating material 226 are inclined forwardly at an angle of 37 degrees relative to the longitudinal axis of fiber 217. Other angles can be used for surface 218 and coating material. The light reflection characteristics of metal film and dielectric coating materials are not sensitive to the angle at the distal end of fiber 217. Angles outside of the range of 37 to 45 degrees can be used for coating material 226 to reflect light laterally relative to the longitudinal axis of optical fiber 217. When the angle of coating material 226 is 37 degrees, the reflected light will emerge at approximately 70 degrees in air with an associated divergence. A tubular layer of polymer material 220 surrounds cladding 219 to protect fiber 217 and cladding 219. A jacket of plastic material, such as Teflon, surrounds polymer material 220. A transparent capsule or tubular member 222 having a closed convex curved end 223 is located about the distal end of fiber 217 within a gas chamber 224. The distal end of fiber 217 and coating material 226 is surrounded by gas chamber 224. Member 222 is a silica cylindrical tubular member made of silica material the same as or similar to the silica material of fiber 217.

The distal end of fiber 217 is united at 225 to the inside wall 227 of tubular member 222. The materials of the fiber and tubular member are fused with localized heat. The heat, 1400° to 1700° C., required to cause the fusion of the silica materials of fiber 217 and tubular member 222 is supplied by a laser beam, as shown in FIG. 7. The laser used to fuse the silica of fiber 217 to tubular member 222 can be a carbon dioxide laser.

Probe 233 is made by providing an elongated optical fiber 217 adapted to be coupled to a laser used to direct a laser beam or light along the fiber. The fiber has a silica fiber core enclosed within a silica cladding 219. The fiber core and cladding 219 are covered with a plastic sleeve 220 and a plastic jacket 221. The coating material 226 is secured to surface 218. The entire surface 218 is covered with a film of layer of coating material 226. The distal end of fiber 217 is cut at a selected angle, such as an angle of 37 degrees relative to the longitudinal axis of fiber 217 to provide inclined oval surface 218. A tubular member 222, having a closed end 223 and an air chamber 224, is provided to accommodate and support the distal end of fiber 217. The distal end of fiber 217 is inserted through the open end of tubular member 222 into air chamber 224. Tubular member 222 is then secured to sleeve 220 and jacket 221 with coating material 226 spaced from the inside of closed end 223 of member 222. A heat source, such as a carbon dioxide ($CO_2$) laser beam, is used to heat the silica at the end of fiber 217 opposite surface 218 and adjacent material of tubular member 222 to unite or fuse fiber 217 to member 222 in area 225 opposite surface 218. As seen in FIGS. 15 and 17, fused area 225 has a circumferential length of about 100 degrees. Other circumferential or arcuate lengths of fused area 225 can be used to connect fiber 217 to member 222. The progress of the fusing process is monitored visually or by instrumentation.

Referring to FIGS. 16 and 17, light or laser beam 230 generated by a laser (not shown) axially propagates down fiber 217. When light 230 encounters coating material 226, it redirects or reflects light energy indicated by arrows 231. The angle of coating material 226, being 37 degrees relative to the longitudinal axis of fiber 217, results in reflection of light 230 as redirected light 231 at an angle of approximately 70 degrees relative to the longitudinal axis of fiber 217. When coating material 226 is positioned at angles different than 37 degrees, light 230 will be redirected laterally at angles related to the different angle or positions of coating material 226. Light 230 is efficiently redirected laterally through fiber 217, the fused area 225 and member 222. Fiber 217, fused area 225 and member 222, being of the same silica materials, do not produce changes in the refractive indices and thereby do not produce reflected light nor secondary refractive light. Reflections that stem from multiple changes in the refractive indices in the exit path of the laser beam are eliminated. Probe 213 is a reliable means to efficiently deliver high energy laser light that is essentially not wavelength selective.

Referring to FIGS. 18–24, there is shown a second modification of the side-firing laser optical fiber probe of the invention, indicated generally at 313. Probe 313 has an elongated flexible optical fiber 317 terminating in two outwardly and forwardly inclined end surfaces 315 and 318. Fiber 317 has a silica fiber core surrounded with a doped fused silica cladding 319. Surfaces 315 and 318 diverge outwardly and forwardly whereby the distal end of fiber 317 has a V-shaped groove. A diamond-tipped abrasive tool, a carbon dioxide ($CO_2$) laser tightly focused or excimer laser can be used to polish surfaces 315 and 318. Surfaces 315 and 318 can be covered with coating material, such as a gold or silver film or dielectric material. Surfaces 315 and 318 are inclined forwardly at an angle of 37 degrees relative to the longitudinal axis of fiber 317. Other angles can be used for surfaces 315 and 318. When the angles of surfaces 315 and 318 are 37 degrees, the reflected light will emerge at approximately 70 degrees in air with an associated divergence. Tubular cladding 319 surrounds fiber 317 to protect the fiber and maintain the laser light within fiber 317. A jacket 321 of plastic material surrounds cladding 319 and a sleeve 320 of plastic material. A transparent capsule or tubular member 322 is located about the distal end of fiber 317 to enclose the distal end of fiber 317 within a gas chamber 324. The gas is air. The distal end of fiber 317 is surrounded by chamber 324. Member 322 is a silica cylindrical tubular member made of silica material the same as or similar to the silica material of fiber 317.

Figure 20:
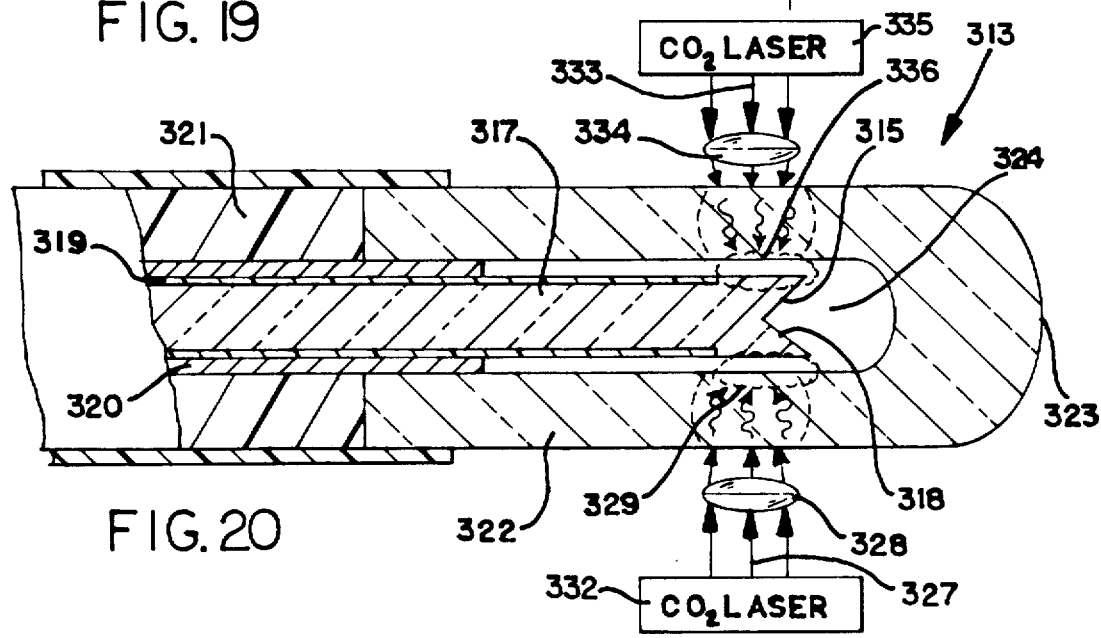
FIG. 20 is a view similar to FIG. 18 showing the fusing of the fiber to the tubular member adjacent the inclined surfaces at the distal end of the fiber.
Figure 30:
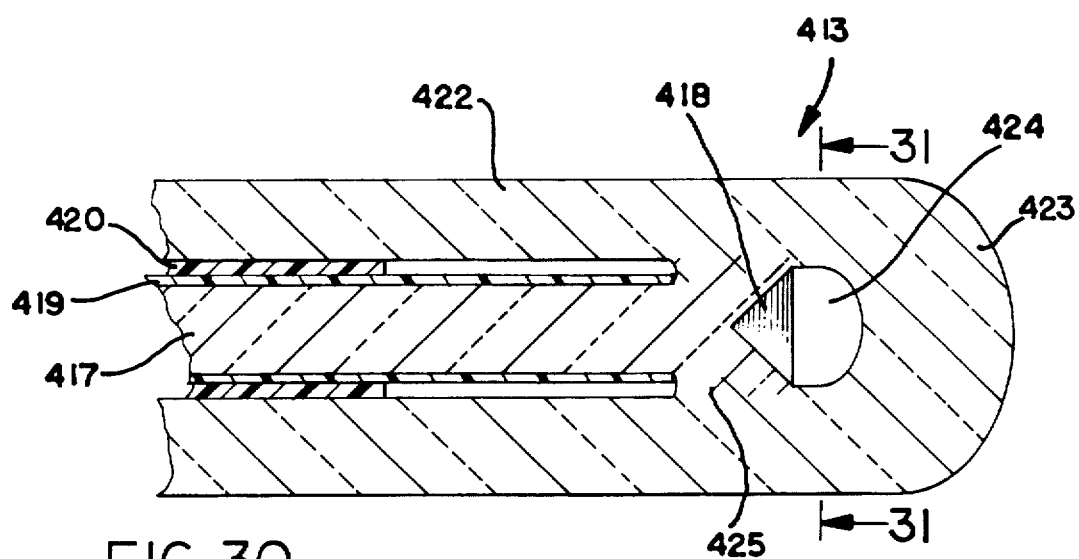
FIG. 30 is a sectional view taken along the line 30—30 of FIG. 29.

The distal end of fiber 317 is united at 325 and 336 to the inside wall of tubular member 322. The materials of the fiber and tubular member are fused with localized heat. As shown in FIG. 20, the heat in the range of 1400° to 1700° C. required to cause the fusion of the silica materials of fiber 317 and tubular member 322 is supplied by a first laser 332 generating laser beam 327 directed through an optical lens 328 which concentrates the laser beam 327 on the surface of tubular member 322. The heat is conducted through the silica material of tubular member 322 to area 329 opposite surface 318. A second laser beam 333 from a laser 335 is directed through lens 334 to provide localized heat on the surface of tubular member 322 opposite surface 315 provides heat in the range of 1400° to 1700° C. which is applied to tubular member 322 adjacent the end of fiber 317. The heat in area 336 fuses the material of fiber 317 opposite surface 315 to the adjacent side of tubular member 322. A single laser beam can be used to sequentially unite the opposite sides of fiber 317 to adjacent portions of tubular member 322. The silica material within areas 329 and 336 are melted and fused together as shown in FIGS. 22–25. Laser beams 327 and 333 are generated with carbon dioxide ($CO_2$) lasers 332 and 335. Other types of laser energy and heat sources can be used to unite the opposite portions of the end of fiber 317 to the inside of tubular member 322.

Probe 333 is made by providing an elongated optical fiber adapted to be coupled to a laser used to direct a laser beam or light along the fiber. The optical fiber has a silica fiber core enclosed within a fused silica cladding 319 and a sleeve 320 surrounded by a jacket 321. A cutter or similar tool is used to cut a V-shaped groove across the end of fiber 317 to form surfaces 315 and 318. Each surface 315 and 318 has an angle of 37 degrees relative to the longitudinal axis of fiber 317 to provide inclined surfaces 315 and 318. Surfaces 315 and 318 are polished with a diamond-tipped abrasive tool, carbon dioxide ($CO_2$) laser, or excimer laser to provide a smooth and flat surface. A tubular member 322, having a closed convex end 323 and an air chamber 324, is provided to accommodate and support tubular member 322 and prevent separation of tubular member 322 from fiber 317. The distal end of fiber 317 is inserted through the open end of tubular member 322 into air chamber 324. Tubular member 322 is then secured to sleeve 320 and jacket 321 with surfaces 315 and 318 spaced from the inside of closed end 323 of member 322. A first heat source 332, generates a carbon dioxide ($CO_2$) laser beam 327, and is localized on the surface of the tubular member 322 opposite surface 318 to unite or fuse fiber 317 to member 322 in area 329 opposite surface 318. A second heat source 335 generates a laser beam 333 that is localized on the surface of tubular member 322 to unite the silica material of fiber 317 with the adjacent silica material of tubular member 322. As seen in FIGS. 23 and 25, fused areas 325 and 326 each have a circumferential length of about 100 degrees. Other circumferential or arcuate lengths of fused areas 325 and 326 can be used to connect fiber 317 to member 322. The progress of the fusing process is monitored visually or by instrumentation.

Referring to FIGS. 24 and 25, light or laser beam 330 generated by a laser axially propagates down fiber 317. When light 330 encounters a change in refractive index, it redirects a portion of the light energy indicated by arrows 331 and 336. The angles of polished surfaces 315 and 318 being 37 degrees relative to the longitudinal axis of fiber 317 results in almost total internal reflection of light 330 as redirected light 331 and 336 at an angle of approximately 70 degrees relative to the longitudinal axis of fiber 317. Light 331 and 336 is efficiently redirected laterally through fiber 317, the fused areas 325 and 326, and member 322, being of the same silica materials, do not produce changes in the refractive indices and thereby do not produce reflected light nor secondary refractive light. Reflections that stem from multiple changes in the refractive indices in the exit path of the laser beam are eliminated. Probe 333 is a reliable means to efficiently deliver high energy laser light in opposite lateral directions that is essentially not wavelength selective.

Referring to FIGS. 26–32, there is shown a third modification of the side-firing laser optical fiber probe of the invention, indicated generally at 413. Probe 413 has an elongated flexible optical fiber 417 terminating in a recessed inclined cone-shaped surface 418. Fiber 417 has a silica fiber core surrounded with a doped fused silica cladding 419. Surface 418 has a generally recessed cone-shaped polished shape. Surface 418 can be covered with a coating material, such as a gold or silver film or dielectric material. A diamond-tipped abrasive tool, a carbon dioxide ($CO_2$) laser tightly focused or excimer laser can be used to polish surface 418. These polishing methods are examples of polishing technology for polishing surface 418. Other polishing procedures can be used to create the desired surface characteristics on surface 418. Surface 418 is inclined forwardly at an angle of 37 degrees relative to the longitudinal axis of fiber 417. Other angles can be used for surface 418. When the angle of surface 418 is 37 degrees, the reflected light will emerge at approximately 70 degrees in air with an associated divergence. A tubular layer of silica cladding 419 surrounds fiber 417 to protect the fiber and maintain the laser light within fiber 417. Cladding 419 is covered with a plastic sleeve 420 surrounded with a plastic jacket, such as jacket 21. A transparent capsule or tubular member 422 having a closed convex curved end 423 is located about the distal end of fiber 417 to enclose the distal end of fiber 417 within a gas chamber 424. The gas is air. The distal end of fiber 417 is surrounded by chamber 424 and spaced from the inside of end 423. Member 422 is a silica cylindrical tubular member made of silica material the same as or similar to the material of fiber 417.

The distal end of fiber 417 is united at 425 to the inside annular wall of tubular member 422. The silica materials of fiber 417 and tubular member 422 are fused with localized heat. As shown in FIG. 28, the heat required to cause the fusion of the silica materials of fiber 417 and tubular member 422 is supplied by a laser 432 which generates a laser beam 427. Laser beam 427 is directed through an optical lens 428 which concentrates the laser beam 427 on the surface of tubular member 422 opposite surface 418. A second laser 435 generating a laser beam 433 is used to unite the silica material in area 436. One or more laser beams travelling around tubular member 422 can be used to unite annular portions of fiber 417 and tubular member 422 together. Alternatively, probe 413 can be rotated about its longitudinal axis whereby laser beams 427 and 433 unit adjacent annular portions of fiber 417 to tubular member 422. The silica material within annular areas 429 and 436 are melted and fused together as shown in FIGS. 30–33. Laser beams 427 and 433 are carbon dioxide ($CO_2$) laser beams. Other types of laser energy and heat sources can be used to unite the end of fiber 417 to the inside of tubular member 422.

Probe 433 is made by providing an elongated optical fiber adapted to be coupled to a laser used to direct a laser beam or light along the fiber. The optic fiber has a silica fiber core 417 enclosed within a fused silica cladding 419 and a plastic sleeve 420. A plastic jacket 421 covers sleeve 420. A cone-shaped recess having a cone surface 418 is cut or drilled into the distal end of fiber 417. A laser generating a laser beam can be used to make the cone-shaped recess in the distal end of fiber 417. The cone-shaped surface 418 has an angle of 37 degrees relative to the longitudinal axis of fiber 417 to provide inclined cone surface 418. Surface 418 is polished with a diamond-tipped abrasive tool, carbon dioxide ($CO_2$) laser, or excimer laser to provide a smooth and flat surface.

Figures 31, 33:
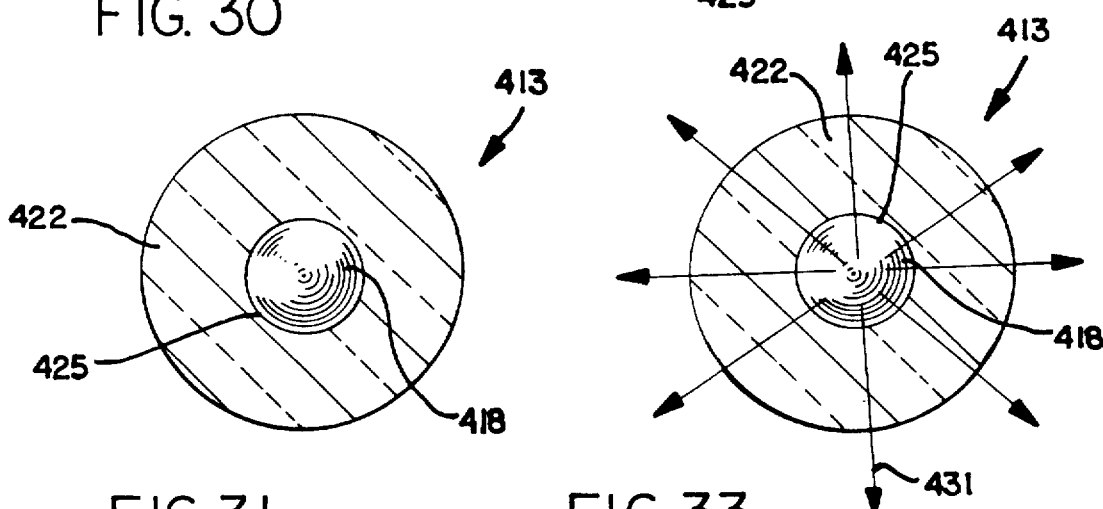
FIG. 31 is a sectional view taken along the line 31—31 of FIG. 30.
FIG. 33 is a sectional view taken along the line 33—33 of FIG. 32.

A tubular member 422, having a closed end 423 and air chamber 424, is provided to accommodate and support the distal end of fiber 417. The distal end of fiber 417 is inserted through the open end of tubular member 422 into air chamber 424. Tubular member 422 is then secured to sleeve 421 with surface 418 spaced from the closed end 423 of member 422. Heat sources, such as carbon dioxide ($CO_2$) laser beams from lasers 432 and 435 are localized on the outer surface of tubular member 422 opposite surface 418 to unite or fuse fiber 417 to member 422 in area 429 opposite surface 418. As seen in FIGS. 31 and 33, fused area 425 has a circumferential length of 360 degrees. Probe 413 and laser beams 427 and 433 can be rotated relative to each other to angularly unite fiber 417 with tubular member 422.

An alterative method of annularly fusing the distal end of fiber 417 to tubular member 422 is to provide a tubular member having an open distal end. Laser light from a laser is directed through the open end of the tubular member to annularly unite or fuse the distal end of the fiber 417 to the inside wall of the tubular member. The laser light is also used to cut a generally cone-shaped recess in the distal end of the fiber 417 and providing a polished cone-shaped surface. Coating materials, such as metal films or dielectric materials, can be applied to the cone-shaped surface. The open end of the tubular member is closed by subjecting the distal end of the tubular member to heat from laser light generated by a laser. The progress of the fusing process is monitored visually or by instrumentation.

Figure 32:
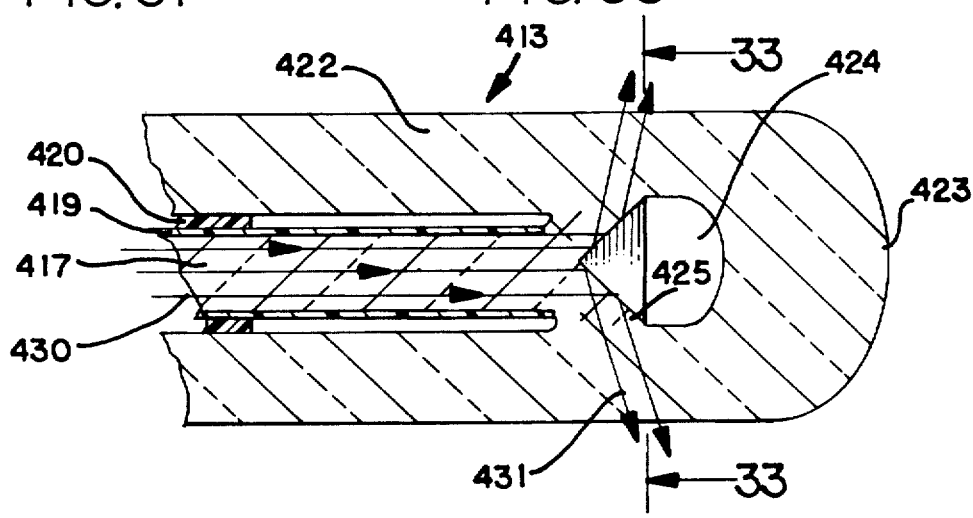
FIG. 32 is a sectional view similar to FIG. 30 showing the fiber subjected to laser light and the lateral redirection of the laser light.

Referring to FIGS. 32 and 33, light or laser beam 430 generated by a laser axially propagates down fiber 417. When light 430 encounters a change in refractive index, it redirects the light energy laterally of the longitudinal axis of fiber 417 indicated by arrows 431. The angle of polished surface 418 being 37 degrees relative to the longitudinal axis of fiber 417 results in almost total internal reflection of light 430 as redirected light 431 at an angle of approximately 70 degrees relative to the longitudinal axis of fiber 417. Light 431 is efficiently redirected laterally through the distal end of fiber 417, the fused area 425 and member 422. Light 431, as seen in FIG. 33, is directed laterally 360 degrees around probe 413. Fiber 417, fused area 425 and member 422, being of the same silica materials, do not produce changes in the refractive indices and thereby do not produce reflected light nor secondary refractive light. Reflections that stem from multiple changes in the refractive indices in the exit path of the laser beam are eliminated. Probe 413 is a reliable means to efficiently deliver high energy laser light 360 degrees laterally of the probe that is essentially not wavelength selective.

There have been shown and described several embodiments of the laser optic fiber probe and methods of making the probe of the invention. It is understood that modifications, changes in the structures, arrangement of structures, materials and methods of making the probe can be made by one skilled in the art without departing from the invention. The invention is defined in the following claims.

I claim:

1. A probe for transmitting laser light and redirecting the light laterally relative to the probe comprising: an optical fiber having a core and means surrounding said core for protecting said core, said fiber having a distal end section terminating in an end having at least one forwardly inclined surface, a tubular member surrounding the distal end section providing a gas chamber for the distal end section and inclined surface, said tubular member having a close end to confine the distal end section and inclined surface to said gas chamber thereby providing a gas interface with said surface, said distal end section having a portion thereof generally opposite the inclined surface united to a portion of the tubular member, said portions of the distal end section of the fiber and tubular member being fused together to provide continuous material through which the light is redirected from said inclined surface, whereby light from a laser propagated down the optical fiber is redirected laterally from said inclined surface through the united portions of the fiber and tubular member and laterally of the probe.

2. The probe of claim 1 wherein: the portion of the distal end section and the portion of the tubular member are fused together with localized heat.

3. The probe of claim 1 wherein: said surface is inclined at an angle of between 37 to 45 degrees relative to the longitudinal axis of the fiber.

4. The probe of claim 1 wherein: said surface is a polished surface.

5. The probe of claim 1 wherein: the means for protecting said core includes fused silica means surrounding said core.

6. The probe of claim 1 wherein: the end of the distal end section has a plurality of inclined surfaces, said distal end section having a portion generally opposite each inclined surface united to separate portions of the tubular member whereby light from a laser propagated down the fiber is redirected laterally from each of said surfaces through the united portions of the fiber and tubular member and laterally out of the probe.

7. The probe of claim 6 wherein: the portions of the distal end section and the separate portions of the tubular member are fused together to provide continuous material through which the light is redirected from said inclined surfaces.

8. The probe of claim 1 wherein: the distal end section has a V-shaped groove with two inclined surfaces, said distal end section having opposite portions united to separate portions of the tubular member whereby light from a laser propagated down the optical fiber is redirected laterally from each of said surfaces through the united portions of the fiber, and tubular member and laterally of the probe.

9. The probe of claim 8 wherein: the opposite portions of the distal end section and the separate portions of the tubular member are fused together to provide continuous material through which the light is redirected from said two inclined surfaces.

10. The probe of claim 1 wherein: the end of the distal end section has a cone-shaped recess with a cone surface, said distal end section having an annular portion thereof surrounding said cone surface united with an annular portion of the tubular member whereby light from a laser propagated down the optical fiber is redirected laterally from the cone surface through the united annular portions of the fiber and tubular member and laterally of the probe.

11. The probe of claim 10 wherein: the annular portion of the distal end section and the annular portion of the tubular member are fused together to provide continuous material through which the light is redirected from said cone surface.

12. The probe of claim 10 wherein: the cone surface is a polished cone surface.

13. The probe of claim 10 wherein: the cone surface has an angle of between 37 to 45 degrees relative to the longitudinal axis of the fiber.

14. A probe for transmitting laser light and redirecting the light laterally relative to the probe comprising: an optical fiber having silica fiber core, means surrounding said fiber core for protecting said fiber core, said core having a distal end section terminating in an end having a forwardly inclined surface, a silica capsule surrounding the distal end section and secured to said means providing a gas chamber for the distal end section and inclined surface, said capsule having a closed end to confine the distal end section and inclined surface to said gas chamber thereby providing a gas interface with said surface, said distal end section having a portion thereof generally opposite the inclined surface united to a portion of the capsule by fusing the silica of the fiber core with the silica of the capsule whereby light from a laser propagated down the optical fiber core is redirected laterally from said inclined surface through the united portions of the fiber core and capsule and laterally of the probe.

15. The probe of claim 14 wherein: the portion of the distal end section and the portion of the capsule are fused together with localized heat.

16. The probe of claim 14 wherein: said surface is inclined at an angle of between 37 to 45 degrees relative to the longitudinal axis of the fiber core.

17. The probe of claim 14 wherein: the means for protecting said fiber core includes fused silica means surrounding said silica fiber core.

18. The probe of claim 14 wherein: the end of the distal end section has a plurality of inclined surfaces, said distal end section having a portion generally opposite each inclined surface united to separate portions of the capsule whereby light from a laser propagated down the fiber core is redirected laterally from each of said surfaces through the silica of the united portions of the fiber core and capsule and laterally of the probe.

19. The probe of claim 14 wherein: the distal end section has a V-shaped groove with two inclined surfaces, said distal end section having opposite portions united to separate portions of the capsule whereby light from a laser propagated down the fiber core is redirected laterally from each of said surfaces through the silica of the united portions of the fiber core, and capsule and laterally of the probe.

20. The probe of claim 14 wherein: the end of the distal end section has a cone-shaped recess with a cone surface, said distal end section having an annular portion thereof surrounding said cone surface united with an annular portion of the capsule whereby light from a laser propagated down the fiber core is redirected laterally from the cone surface through the silica of the united annular portions of the fiber core and capsule and laterally of the probe.

21. The probe of claim 20 wherein: the cone surface is a polished cone surface.

22. The probe of claim 21 wherein: the cone surface has an angle of between 37 to 45 degrees relative to the longitudinal axis of the fiber core.

23. A probe for transmitting laser light and redirecting the light laterally relative to the probe comprising: an optical fiber having fiber core, means surrounding said fiber core for protecting said fiber core, said core having a distal end section terminating in an end having at least one forwardly inclined surface, coating means secured to and covering said inclined surface operable to redirect laser light laterally relative to the probe, a capsule surrounding the distal end section including the coating means providing a gas chamber for the distal end section and coating means, said distal end section having a portion thereof fused to a portion of the capsule generally opposite the inclined surface whereby light from a laser propagated down the fiber core is redirected laterally from said coating means through the fused portions of the fiber core and capsule and laterally of the probe.

24. The probe of claim 23 wherein: the fiber core and capsule have the same silica materials.

25. The probe of claim 23 wherein: the coating means comprises a metal film secured to and covering said inclined surface.

26. The probe of claim 23 wherein: the coating means comprises a dielectric material.

27. The probe of claim 23 wherein: the distal end section terminates in an end having a single inclined surface, said surface being covered with the coating means.

28. The probe of claim 23 wherein: the fiber core is a silica core, and a fused silica cladding surrounding the silica core.

29. A method of making a probe for transmitting laser light and laterally redirecting the light comprising: providing an elongated optical fiber including a core adapted to be coupled to a laser operable to direct light along said core, forming on the distal end of the fiber an angled optical surface for redirecting said light so that the light exits the fiber laterally of the fiber, enclosing the distal end of the fiber including the surface in a tubular member having a closed end to locate the surface in an enclosed gas chamber to provide a gas interface with the surface, and uniting a portion of the fiber opposite the surface to a portion of said tubular member with localized heat to fuse the portion of the fiber opposite the surface to the tubular member whereby light from a laser propagated down the fiber is redirected laterally from said surface through the united portions of the fiber and tubular member and laterally out of the probe.

30. The method of claim 29 wherein: the distal end of the fiber is cut at an angle of between 37 to 45 degrees relative to the longitudinal axis of the fiber.

31. The method of claim 29 wherein: the surface is polished.

32. The method of claim 29 wherein: the heat is light energy generated with a carbon dioxide laser.

33. The method of claim 29 wherein: the distal end of the fiber is cut to provide separate surfaces, and joining a first portion of the fiber opposite one surface to the tubular member and a second portion of the fiber opposite the other surface to the tubular member whereby the light from a laser propagated down the fiber is redirected laterally from each surface through the joined portions of the fiber and tubular member and laterally of the probe.

34. The method of claim 33 wherein: the distal end of fiber is cut to provide each surface with an angle of between 37 to 45 degrees relative to the longitudinal axis of the fiber core.

35. The method of claim 33 wherein: each surface is polished.

36. The method of claim 33 wherein: the portions of the fiber core opposite the surfaces are joined to the tubular member with localized heat to fuse the portions of the fiber core opposite the surfaces to the tubular member.

37. The method of claim 33 wherein: the heat is light energy generated with a carbon dioxide laser.

38. A method of making a probe for transmitting laser light and laterally redirecting the light out of the probe comprising: providing an elongated optical fiber including a core adapted to be coupled to a laser operable to direct light along said fiber, said fiber having a distal end, cutting a recess with a cone surface in the core in the distal end of the fiber, joining an annular portion of the fiber opposite the cone surface to an annular portion of a tubular member whereby light from a laser propagated down the fiber core is redirected laterally from said cone surface through the joined annular portion of the fiber and tubular member and laterally out of the probe, and enclosing the distal end of the fiber including the cone surface in a tubular member having a closed end to locate the cone surface in an enclosed gas chamber to provide a gas interface with the cone surface.

39. The method of claim 38 wherein: the distal end of the fiber core is cut to provide the cone surface with an angle of between 37 to 45 degrees relative to the longitudinal axis of the fiber core.

40. The method of claim 38 wherein: the cone surface is polished.

41. The method of claim 38 wherein: the annular portion of the fiber is joined to the annular portion of the tubular member with localized heat to fuse the annual portion of the fiber opposite said cone surface and the annular portion of the tubular member.

42. The method of claim 41 wherein: the heat is light energy generated with a carbon dioxide laser.

43. A method of making a probe for transmitting laser light and laterally redirecting the light comprising: providing an elongated optical fiber having a core adapted to be coupled to a laser operable to direct light along said core, forming at least one inclined surface on the distal end of the fiber, coating the inclined surface with a coating material operable to redirect the light from the fiber laterally of the probe, enclosing the distal end of the fiber including the coating material in a capsule having a gas chamber and a closed end to locate said coating material within the gas chamber, and uniting a portion of the fiber opposite the surface to a portion of said capsule with heat to fuse the portions of the fiber and capsule together whereby light from a laser propagated down the fiber is redirected laterally from said coating material through the united portions of the fiber and capsule and laterally out of the probe.

44. The method of claim 43 wherein: the inclined surface is coated with a metal film.

45. The method of claim 43 wherein: the inclined surface is coated with dielectric material.

* * * * *